: : : : : : US005163902A

United States Patent [19]
Lynn et al.

[11] Patent Number: 5,163,902
[45] Date of Patent: Nov. 17, 1992

[54] PATIENT FLUID MANIFOLD

[75] Inventors: Lawrence A. Lynn, Columbus, Ohio; James R. Longacre, 3621 Littledale Rd., Kensington, Md. 20895

[73] Assignee: James R. Longacre, Arlington, Va.

[21] Appl. No.: 581,699

[22] Filed: Sep. 13, 1990

[51] Int. Cl.⁵ ............................................ A61M 37/00
[52] U.S. Cl. ........................................ 604/86; 604/283
[58] Field of Search ..................................... 604/80–88, 604/192, 263, 258, 283; 28/DIG. 12, DIG. 15

[56] References Cited

U.S. PATENT DOCUMENTS

| | | | |
|---|---|---|---|
| 3,074,542 | 1/1963 | Myerson et al. | 206/43 |
| 3,834,386 | 9/1974 | Sisley | 604/86 X |
| 4,048,995 | 9/1977 | Mittleman | 604/86 |
| 4,121,585 | 10/1978 | Becker, Jr. | 604/86 |
| 4,252,117 | 2/1981 | Sheehan | 604/86 |
| 4,560,378 | 12/1985 | Weiland | 604/83 |
| 4,915,688 | 4/1990 | Bischof et al. | 604/83 |
| 4,921,119 | 5/1990 | Villaveces | 248/314 |
| 4,966,582 | 10/1990 | Sit et al. | 604/86 |

FOREIGN PATENT DOCUMENTS 1907296 9/1969 Fed. Rep. of Germany ...... 604/258

Primary Examiner—John D. Yasko
Assistant Examiner—Adam J. Cermak
Attorney, Agent, or Firm—Longacre & White

[57] ABSTRACT

A manifold for fluid connection of a plurality of sources of fluid for a patient in which a number of inlet ports on the upper surface of a housing communicate with a lower outlet port by passages or bores which merge to a single passages or bore. The ports are respectively occluded by elastomeric sealing members adapted to be penetrated by a needle or cannula. Preferably, the inlet ports are symmetrical or coincident with an axis so the distance travelled by the fluid from each source is substantially the same.

31 Claims, 4 Drawing Sheets

PATIENT FLUID MANIFOLD

BACKGROUND OF THE INVENTION

The invention relates to a fluid manifold for coupling a plurality of fluid sources to a patient.

In the hospital environment, particularly in intensive care, patients typically receive various kinds of fluids intravenously through a catheter. Some of the fluids provide nutrients, others replace blood and blood components, while yet others are drugs. Some of the fluids may be supplied continuously for a matter of days while others may be supplied for only a short period of time.

Typically, all of the fluid sources are coupled to a single catheter by means of various "Y" connectors and the like. The result is too often a tangle of tubing adjacent and sometimes on or under the patient which is untidy, confusing and can even lead to error. Moreover, it is very easy for some of the sources to become pinched or even disconnected from the patient without the nurse or attending doctor immediately noticing and remedying the disconnection. Blood may also be withdrawn through the same catheter for testing increasing the confusion and potential for error.

This problem is to a considerable extent alleviated by a unique universal connector as described in a co-pending application entitled "Universal Intravenous Connector with Needle Protection", Ser. No. 07/509,639, filed Apr. 17, 1990 now abandoned (the disclosure of which is hereby incorporated by reference). This connector permits by easy and reliable one handed motion any syringe or tubing to be coupled to virtually any junction which is occluded by a septum or the like. This universal connector thus provides greater security that inadvertent disconnection will not take place and at the same time provides protection for the nurse and others in the environment of the bedside from possible needle stick.

However, the universal connector does not by itself provide improved organization of the tubes supplying the fluid nor does it remove the possibility that some of the tubes may be pinched off to interrupt the supply of fluid, or may be inadvertently connected wrongly, or may even be disconnected.

One approach which has been proposed to better organize the flow of fluid from the various sources to the patient is to provide a manifold with input valves such as stopcocks, which must be manually operated in order to interrupt and resume the flow of the fluid. For example, the recently issued U.S. Pat. No. 4,915,688 to Bischof, describes a manifold arrangement of this type. The need for stopcocks and the bulky shape result in a device which is complex and expensive. For these reasons, previous manifolds have not been wholly satisfactory nor do they completely answer the problems described above.

Such manifolds further are typically arranged with the stopcocks in a line. While this may make it easier for the nurses to keep track of tubes, it also results in a bulky configuration which is difficult to mount. Further, should a source run dry and the nurse neglect to close the stopcock the tendency to backflow may be enhanced when the input from the empty source is immediately adjacent one which is at full pressure.

As a practical matter, such a manifold cannot be reused; it must be disposable. Further, in today's hospital environment, cost is extremely important. Thus, it is vital that any manifold intended for general use be not only easy to use and reliable, but also be inexpensive and simple to manufacture.

The present invention relates to a unique disposable manifold which can be attached as desired by the nurse at any convenient bedside location and therefore is universally adaptable to almost any bedside set up and any hospital bed. The manifold further can be positioned at a height and at a position chosen by the nurse to suit her own height and work habits.

Equally important, the manifold is simple, reliable and relatively inexpensive to manufacture.

In the unique manifold of the present invention, a housing, preferably formed as a single molded plastic, is provided on an upper extending surface with a plurality of separate inlet ports. These inlet ports communicate to internal passages or bores extending downward within the housing and merging within the housing into a single passage or bore communicating to a single outlet port. From the outlet port a tube extends to a catheter adapted for supplying the fluid exiting the outlet port to the patient.

At least one and preferably all of the inlet ports are occluded by an elastomeric member such as a septum which can be penetrated by a needle or blunt cannula and which maintains the interior passages or bores sterile. The chances of backflow is also minimized because conditions creating backward flow through a needle penetrating a septum are unlikely to occur.

Each inlet port is preferably formed as an open ended tube extending upwardly from an upper surface which in a first embodiment is both circular and planar. The above described universal connector can readily and effectively connect to such an inlet port which can also receive a needle from a conventional syringe or other device. The connector, syringe or other device extends through the occluding elastomeric material so that the fluid passes downward through tube into the associated bore and then into the merged bore, and ultimately to the patient via the outlet port. Preferably, flow takes places by gravity, but pumps can be employed if desired.

Preferably the distance travelled by the fluid from each of the inlet ports to the single outlet port is substantially the same. Thus, the size of the manifold is minimized, as is the tendency for backflow since each inlet tube is closer to the outlet, and above the outlet, than to the other inlet tubes. In one embodiment, the inlet ports are symmetrically disposed about an axis with one of the tubes coincident with that axis and the axis likewise defining the axis of the outlet tube.

It is common in the hospital environment for a fluid to be discontinued for some time and then reconnected. According to a further aspect to the present invention, a plurality of needle stations are provided on the exterior surface of the housing in which the needle or connector from a source can be temporarily stored for some time. Preferably, these stations are provided on the outside of the housing between the inlet and outlet ports so that they cannot be confused with inlets. Moreover, the housing is preferably transparent so it will be perfectly apparent by visual inspection which are the inlets and which are the "Needle Minding" stations. The stations can be given a color such as yellow, while remaining transparent, to visually differentiate them even more from the ports. This kind of station is further described in a co-pending application entitled, "Needle Protection Station", Ser. No. 07/515,466 filed Apr. 27, 1990 (the disclosure of which is incorporated herein by reference).

According to a further aspect of the present invention, the housing is removably attachable, for example, by a hook and loop pile fastener such as VELCRO or the like, to any place in the bedside environment chosen by the nurse. Preferably, one patch of VELCRO is attached to a flat surface on the housing between the inlet ports and the outlet port. The VELCRO patch matches a similar patch which can be placed by the nurse anywhere in the bedside environment most convenient to the nurse. The second VELCRO patch is preferably supplied in a package with the manifold so the nurse can attach it whenever the nurse wants. A suitable adhesive is preferably provided on the back of this second patch for that purpose. The manifold may be attached to the patient under some circumstances.

According to another embodiment the manifold is formed with the occluded tubes in line to serve nurses who prefer and are accustomed to the linear manifolds now in use. Preferably, the outlet tube is arranged so that the distance from each inlet tube to the outlet tube is substantially the same and the outlet tube is located below the inlet tubes.

According to yet another embodiment a valve member is provided in at least one and preferably all of the inlet tubes which valve members can be manually rotated to open and close any inlet port without removing the connector or other device penetrating the septum. One suitable valve is formed by a hollow rotatable tube occluded by the elastomeric member with an opening at the bottom which is alignable with the interior passage or bore and which can be rotated out of alignment.

Many other objects and purposes of the invention will be clear from the following detailed description of the drawings.

DETAILED DESCRIPTION OF THE DRAWINGS

Figure 1:
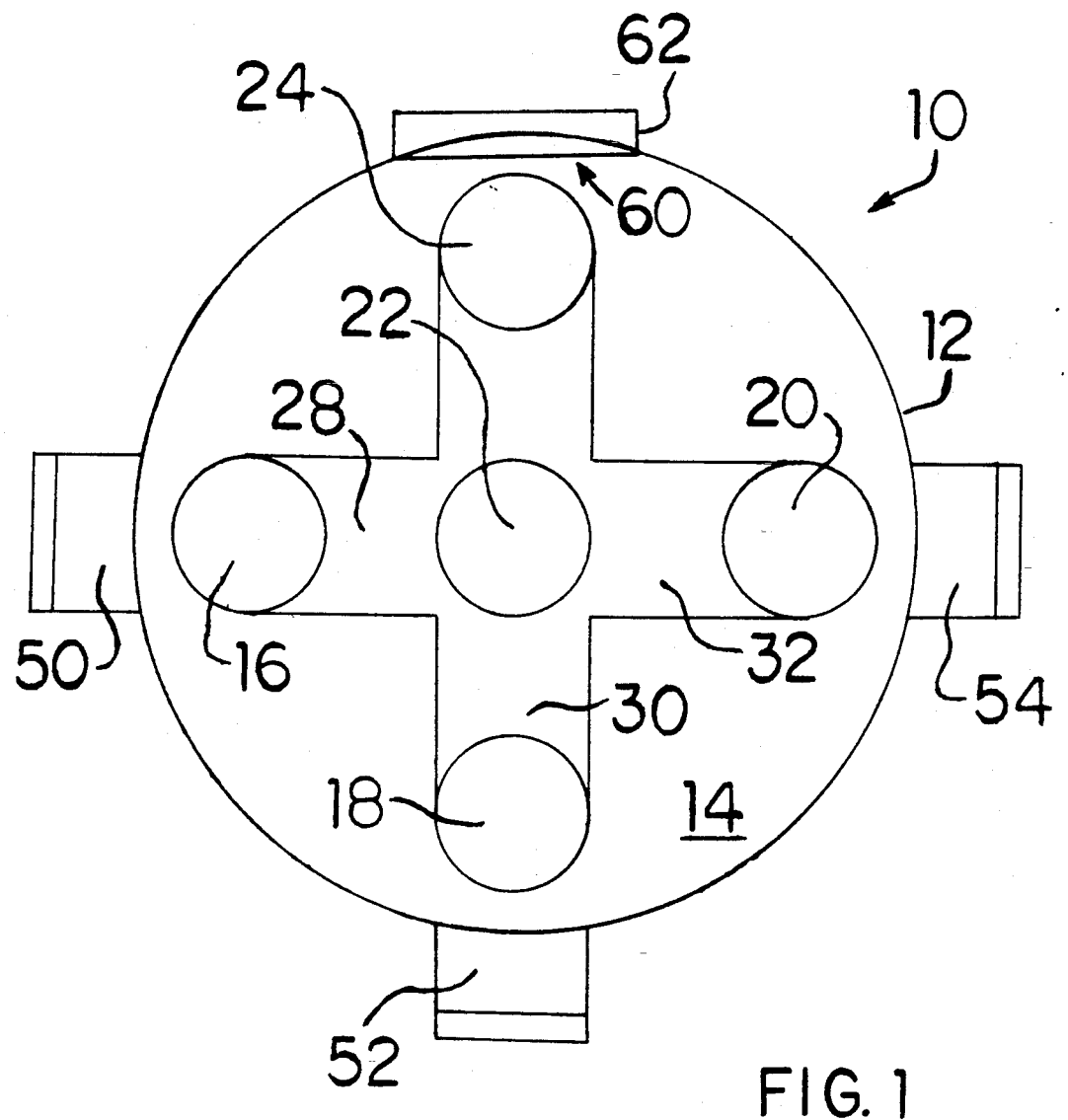
FIG. 1 shows a side view of a first embodiment of the drawing in which a tube and catheter are permanently fixed to the output port.
Figure 2:
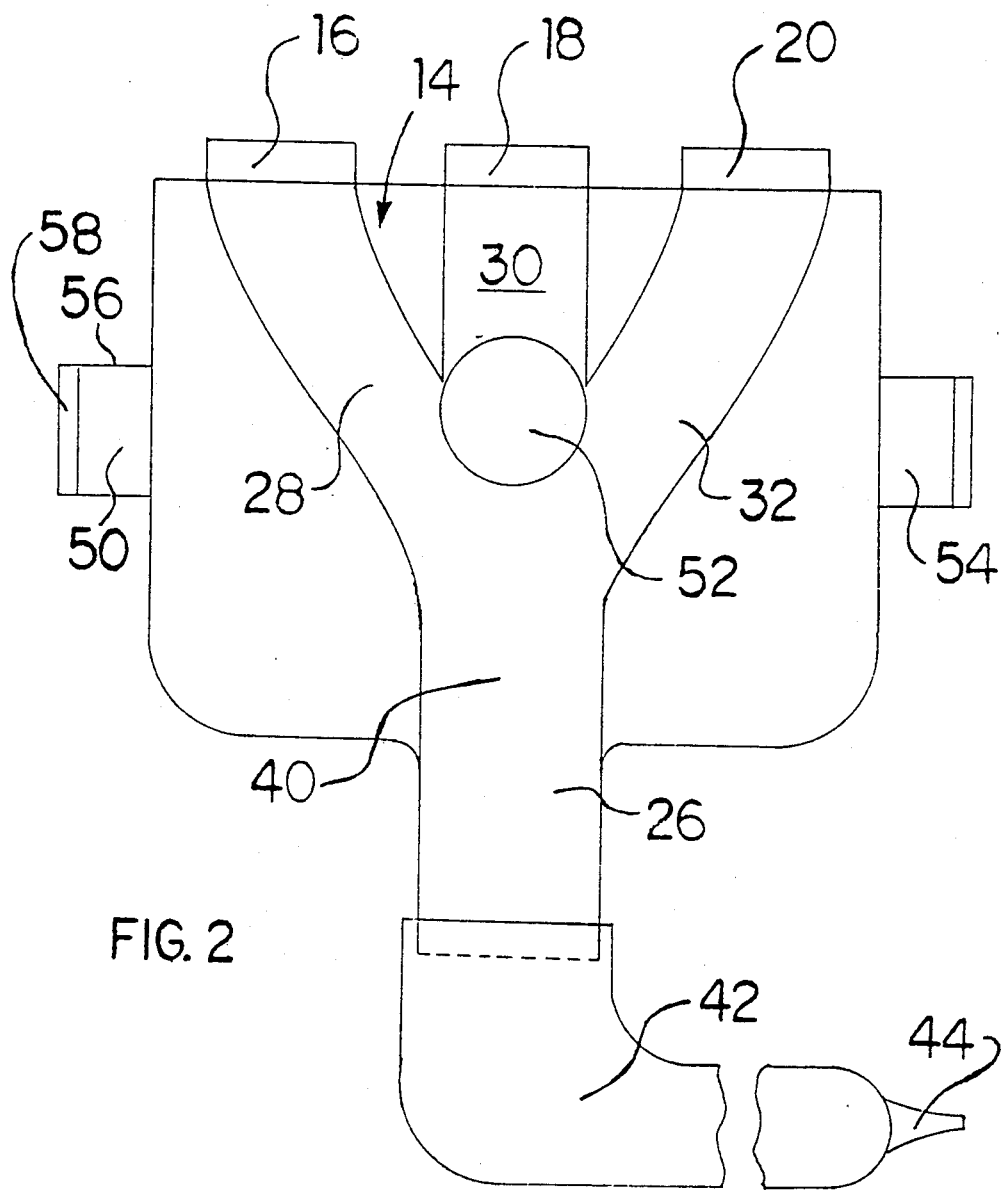
FIG. 2 shows a top view of the embodiment of FIG. 1.

Reference is now made to FIGS. 1 and 2 which illustrate a first embodiment of the present invention. Manifold 10 is formed of a housing 12 which is of a clear single molded plastic. On an upper extending surface 14 of housing 12 are provided five inlet ports 16, 18, 20, 22 and 24. Only inlet ports 16, 18 and 20 can be seen in FIG. 2 since ports 22 and 24 are hidden behind port 18 in that view. The inlet ports 16, 18, 20 and 24 are symmetrical about an axis which also coincides with the axis of inlet port 22. Each of the ports is formed by an open ended tube extending upward from the surface 14.

The respective inlet ports each communicate to an internal passage or bore extending within housing 12 to an outlet port 26 opposite surface 14. As can be seen in FIG. 1, inlet port 16 connects to a internal bore or passage 28, inlet port 18 to a passage 30 and inlet port 20 to a passage 32. The passages connecting to inlet ports 22 and 24 are similarly hidden in FIG. 1. In the embodiment of FIG. 1, these bores are formed by molding, but alternatively, the housing may be hollow with separate flexible or inflexible elements therein forming the respective passages. The exterior surface of housing 12 tapers inwardly in the direction of the outlet port 26.

The molded plastic housing need not be, and is preferably not, solid in the regions between the internal bores and exterior surface. Much of the space can be open so long as the bores remain sealed from the atmosphere and the housing retains sufficient rigidity to avoid breakage.

All the passages from the respective inlet ports between housing surface 14 and outlet port 26 merge into a single bore 40 coincident with the above mentioned axis. Thus, the distance which the fluid travels from each of the respective inlet ports to the outlet port 26 is substantially the same.

FIG. 1 is not a cut away view, but rather the housing is preferably formed of transparent plastic so that the nurse can readily observe that the fluid is indeed flowing as desired through each of the respective passages and can see readily as well the difference between the stations at which needles or the like can be temporarily "minded" or stored and the respective inlet ports.

In the embodiment of FIG. 2, a flexible line 42 is permanently connected to outlet port 26 and bears at its other end a catheter 44 for direct connection to a patient. Thus, the manifold 10, line 42 and catheter 44 can be provided to the nurse as a single sterilized unit. Since the inlet ports are sealed by septums, the interior bores remain sterile after the manifold has been removed from the sterile packaging and until use. Alternatively, the catheter can be separately coupled to outlet port 26.

A plurality of needle stations are preferably provided around the periphery of housing 12 between surface 14 and outlet port 26. As can be seen in FIG. 2, in this embodiment, three stations 50, 52 and 54 are provided, each formed of an open ended tube extending outward and occluded by an elastomeric member which extends to its dead end. Thus, as shown in FIG. 2, a station 50 is formed of a tube 56 with an elastomeric member 58 extending therein to its dead end and to a sufficient distance for fully receiving any needle to be used with the manifold.

As can be seen in FIG. 1, a flat surface 60 is provided between surface 14 and outlet port 26 and fixed to surface 60 is a conventional VELCRO patch 62 for engaging a similar VELCRO patch placed by the nurse at any desired location in the bedside environment. Thus, the manifold of the present invention can be placed wherever the nurse desires and indeed easily moved by the nurse or by another nurse should the occasion warrant.

Figure 3:
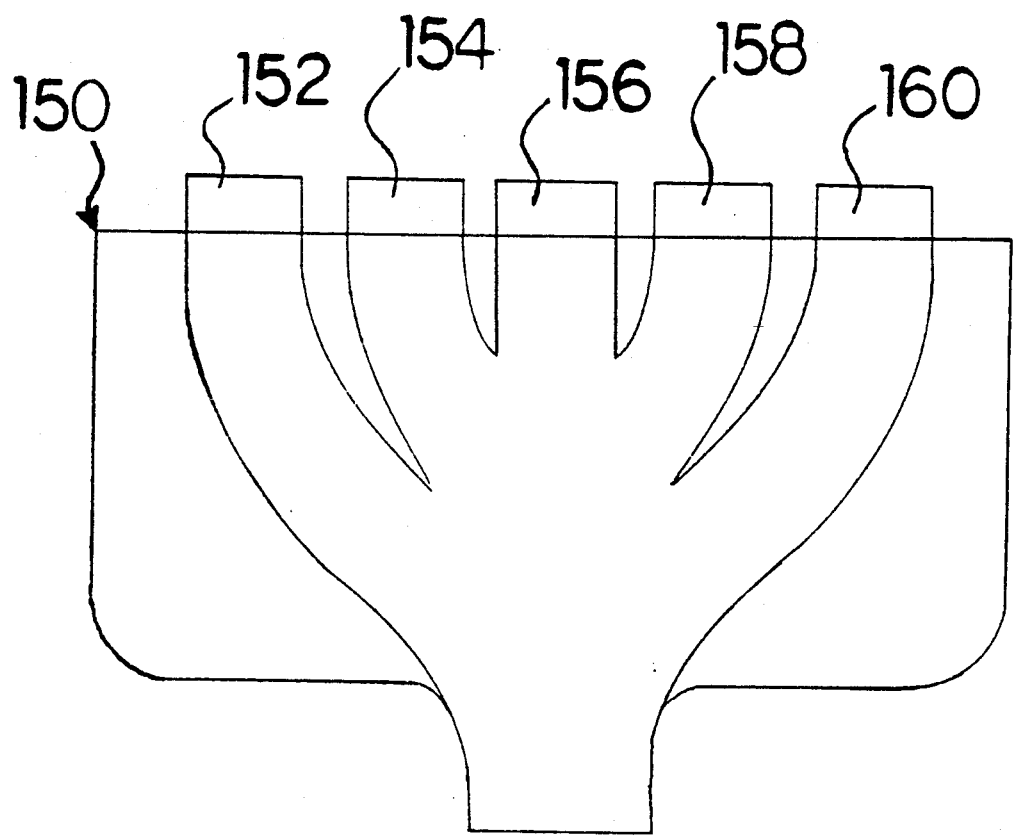
FIG. 3 shows a side view of a second embodiment in which the inlet tubes extend in a line.

FIG. 3 shows a side view of an embodiment which is similar to the embodiment of FIG. 1 and 2 except that the top surface 150 of manifold 152 is not circular, but linear. The tubes 154, 156, 158, 160 and 162 are arranged in a line rather than in a circle. The distance from each inlet tube to the outlet tube 164 is still substantially the same and the outlet tube is arranged to be below the inlet.

Figure 4:
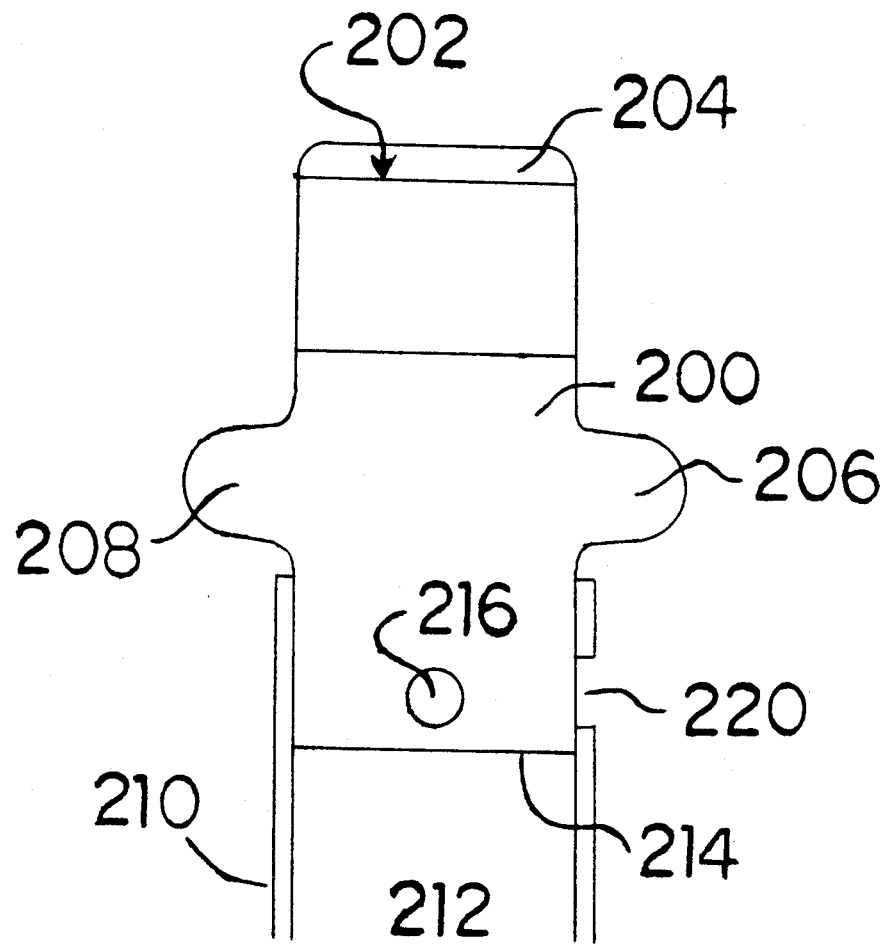
FIG. 4 shows a view of a third embodiment in which the inlet tube operates as a manually operable, rotatable valve.

Reference is now made to FIG. 4 which shows a further embodiment in which the inlet tubes are formed as a separate part from the housing and function as a valve. Thus, the connection between a given source and the patient can be interrupted by manual operation of the valve and without disconnecting the source. Although improved in design and function, the valve operates like a stopcock. Obviously such a manifold is more complex and expensive that the embodiments described about but the additional capability of interruption may be worth the additional expense, at least for some health care providers.

In the drawing only one tube and the associated part of the housing are shown. The other tubes are preferably arranged in the same way, and the housing generally configured as described above.

Tube 200 is preferably a hollow tube of transparent plastic. The open end 202 is occluded by a conventional elastomeric member 204 which can be penetrated by a needle or cannula as described above. Integral portions 206 and 208 extend outwardly from tube 200 near open end 202 to form a handle for rotating tube 200.

Tube 200 is mounted in housing 210 to extend into a bore 212. Tube 200 is easily rotatable within bore 212 but cannot be easily removed. Adjacent the opposite end 214 of tube 200 is an opening 216 communicating to the hollow interior of tube 200. An interior passage of bore 216 has a similar opening 220 into bore 212 so that when openings 220 and 216 are aligned fluid passes from passage 216 into passage 220 which ultimately merges with other passages and conveys fluid to an outlet port as described above. When the openings are not aligned passage is blocked. Detents or stops may be provided if desired to indicate when the connection is open or closed.

Various proposals have been made to incorporate anti-viral or anti-bacterial compositions into elastomers which are then formed as septums. Incorporating such materials into the members occluding the inlet and outlet tubes, and in the needle stations may be desirable.

Many changes and modifications in the above described embodiment of the invention can, of course, be carried out without departing from the scope thereof. For example, provision can be made for withdrawing blood from the patient through the manifold or by an alternative path within the manifold adjacent the outlet port. While the simplicity and ease of manufacture of this manifold militate in favor of single use, the present invention can be reusable, at least for certain applications. Accordingly, that scope is intended to be limited only by the scope of the appended claims.

What is claimed:

1. A manifold for fluid connection of a plurality of sources of fluid for a patient comprising:
   a housing having an upper extended surface with a plurality of inlet ports each adapted for connection to one of said sources, a lower outlet port and conduit means including a plurality of passages each having a centerline, said centerlines intersect at a common point, each of said plurality of passages adapted to carry fluid from one of said input ports to said outlet port; and
   elastomeric sealing means occluding at least one of said inlet ports and adapted to be penetrated by a needle or cannula to supply fluid to that inlet port.

2. A manifold as in claim 1 wherein said inlet ports include at least three ports and wherein the distance travelled by fluid from each of said inlet ports to the outlet port is substantially the same.

3. A manifold as in claim 1 wherein said upper surface is bounded by a edge which is closed.

4. A manifold as in claim 3 wherein said upper surface is planar.

5. A manifold as in claim 4 wherein said upper surface is circular.

6. A manifold as in claim 1 wherein the exterior surface of said housing tapers inwardly in the direction of said outlet port.

7. A manifold as in claim 1 wherein said housing is a unitary plastic molding.

8. A manifold as in claim 1 wherein said inlet ports are each an open ended tube extending upwardly from said surface and communicating each with one of said plurality of passages.

9. A manifold as in claim 1 including a plurality of closed end bores extending into said housing and each occluded by as elastomeric member to provide a station for temporarily storing a needle or cannula.

10. A manifold as in claim 9 wherein said stations are provided on the exterior of said housing between said extended surface and said outlet port.

11. A manifold as in claim 1 further including means for temporarily attaching said manifold to a bedside location.

12. A manifold as in claim 11 wherein said attaching means includes a patch of VELCRO fixed to said manifold for engaging a similar VELCRO patch at a bedside location.

13. A manifold as in claim 12 wherein said housing is provided with a flattened surface between said extended surface and said outlet port to which said VELCRO patch is fixed.

14. A manifold as in claim 1 further including a catheter and a tube connecting said outlet port to said catheter.

15. A manifold as in claim 1 wherein said housing is transparent.

16. A manifold as in claim 1 wherein positions of each of said inlet ports are selected from the group consisting of symmetrical about a centerline of said outlet port and substantially coincident with said centerline of said outlet port.

17. A manifold as in claim 1 wherein each of said ports is occluded by an elastomeric member adapted to be penetrated by a needle or cannula.

18. A molded manifold for connection between a plurality of fluid sources and a patient comprising a housing having a plurality of inlet tubes extending from an exterior surface of said housing, each adapted to be occluded by a septum, an outlet tube extending from said surface and a plurality of internal passages each having a centerline, said centerlines intersect at a common point, and said internal passages extending within said housing from one of said inlet tubes to said outlet tube.

19. A manifold as in claim 18 wherein said manifold is further provided with a plurality of dead end bores extending into said manifold and each adapted to be occluded by an elastomeric member.

20. A manifold as in claim 18 wherein said inlet tubes extend from an upper surface and wherein said manifold tapers inwardly from said upper surface to said outlet tube.

21. A manifold as in claim 18 wherein the surface of said manifold between said inlet tubes and said outlet tube is adapted for attaching said manifold to a surface.

22. A manifold as in claim 18 wherein said manifold is molded of clear plastic.

23. A manifold as in claim 18 wherein said inlet tubes are integral with said housing.

24. A manifold as in claim 18 wherein said housing and inlet tubes are separate.

25. A manifold as in claim 18 wherein said inlet tubes extend from an upper, planar, substantially circular surface.

26. A manifold as in claim 18 wherein the distance fluid travels from each of said inlet tubes to said outlet tube is substantially the same.

27. A manifold as in claim 18 wherein said inlet tubes are symmetrical about an axis and said outlet tube is coincident with said axis.

28. A manifold for coupling a plurality of fluid sources to a patient comprising:

a housing having a plurality of inlet ports, an outlet port, and a plurality of passage means each having a centerline, said centerlines intersect at a common point for connecting said inlet ports to said outlet port; and elastomeric means sealing each of said inlet ports and adapted to be pierced by a needle or blunt cannula and means sealing said outlet port so that passage of contaminants into said passages from the ambient environment is blocked.

29. A manifold as in claim 28 wherein said inlet ports are defined by tubes upwardly extending from an upper surface and said outlet port is defined by a downwardly extending tube.

30. A manifold as in claim 28 wherein said housing is further provided with a plurality of dead end bores extending into said manifold and each adapted to be occluded by an elastomeric member.

31. A manifold as in claim 28 including means for attaching said manifold to an external surface.

* * * * *